US012699864B2

(12) United States Patent
Grajales

(10) Patent No.: US 12,699,864 B2
(45) Date of Patent: Aug. 4, 2026

(54) NEAR FIELD COMMUNICATION ADAPTER TECHNOLOGY FOR PHARMACY, SHOPPING CARTS AND OPHTHALMIC MEDICAL ITEMS

(71) Applicant: Willis Dennis Grajales, Little Elm, TX (US)

(72) Inventor: Willis Dennis Grajales, Little Elm, TX (US)

( * ) Notice: Subject to any disclaimer, the term of this patent is extended or adjusted under 35 U.S.C. 154(b) by 2 days.

(21) Appl. No.: 18/731,306

(22) Filed: Jun. 2, 2024

(65) Prior Publication Data

US 2025/0371301 A1      Dec. 4, 2025

(51) Int. Cl.
*G06K 19/07* (2006.01)
*G16H 20/10* (2018.01)

(52) U.S. Cl.
CPC ......... *G06K 19/0723* (2013.01); *G16H 20/10* (2018.01)

(58) Field of Classification Search
CPC ..... G06K 19/0723; G16H 20/10; G16H 40/67
USPC ........................................................ 235/439
See application file for complete search history.

(56) References Cited

U.S. PATENT DOCUMENTS

| | | | |
|---|---|---|---|
| 9,703,968 B2 * | 7/2017 | Hoyer | ................. G06F 21/6227 |
| 2015/0324681 A1 * | 11/2015 | Mats | ................ G06K 19/07766 235/492 |
| 2017/0076063 A1 * | 3/2017 | Louie | .................... G06Q 10/087 |
| 2017/0091424 A1 * | 3/2017 | Haigh | ..................... H04L 63/08 |
| 2019/0114450 A1 * | 4/2019 | Butler | ................ G06K 7/10198 |

* cited by examiner

*Primary Examiner* — Ahshik Kim

(57) ABSTRACT

Disclosed is a system, method, and apparatus designed to enhance items using Near Field Communication (NFC) radio technology. This includes enhancing medication containers, such as ophthalmic items, eyedrop medication containers, shopping carts, and other pharmacy items. The technology transforms these medical items into secure, contactless mediums for information distribution, data access, and wellness tracking. This integration improves user convenience and medical data management. The system comprises a removable, attachable NFC apparatus that enhances medication containers with NFC capabilities, enabling data programming, retrieval, and health metrics collection. This innovation contributes to the field by converting traditional medication containers or larger containers like shopping carts into multifunctional instruments.

20 Claims, 5 Drawing Sheets

NEAR FIELD COMMUNICATION ADAPTER TECHNOLOGY FOR PHARMACY, SHOPPING CARTS AND OPHTHALMIC MEDICAL ITEMS

RELATED APPLICATIONS

This U.S. Patent Application is a continuation of U.S. patent application Ser. No. 17/468,642, filed on Sep. 7, 2021, titled "Method and System of Using NFC Technology on Eyewear Frames, Eyewear Accessories, and Eye Drop Containers to Link User Devices with Prescriptions and Information," which claims priority to U.S. Provisional Application No. 63/075,827, filed on Sep. 9, 2020, and U.S. Provisional Application No. 63/530,383, filed on Aug. 2, 2023. The entire disclosures of these applications are incorporated herein by reference.

FIELD OF INVENTION

The present invention pertains to the field of adapters with electronic communication technology and healthcare device integration. More specifically, it relates to the development and implementation of Near Field Communication (NFC) technology in healthcare and pharmacy settings, focusing on medication containers and ophthalmic items to facilitate secure, contactless information distribution, retails shopping carts, data access, and wellness tracking. The invention is designed to enhance the functionality of traditional pharmacy items, or medical items through intelligent adapters, transforming them into multi-purpose instruments that enable improved patient convenience, medical data management, and engagement with healthcare services.

SUMMARY OF INVENTION

The present invention addresses the integration of Near Field Communication (NFC) technology adapters into pharmacy items, particularly medication containers and ophthalmic items, to enhance their functionality and utility. This integration facilitates a secure, efficient, and contactless medium for data distribution, access, and wellness tracking.

The core of the invention is a removably attachable NFC adapter apparatus designed to be affixed to medication containers, shopping carts and other pharmacy or medical items. This adapter houses an NFC identification tag that can be programmed with various types of data using an external NFC processing device. The data may include, but is not limited to, medication instructions, dosage information, promotional content, health monitoring metrics, and more. Once programmed, the content and data can be easily retrieved via any external NFC-enabled device.

In practice, the NFC adapter apparatus enables traditional medication containers, shopping carts to serve multiple purposes beyond their conventional use. For instance, a medication bottle can now provide patients with timely medication instructions, reminders for medication intake, and links to digital platforms for managing health care more effectively. Additionally, the system may allow for the integration of promotional and loyalty program functionalities, which can be used by pharmacies, medical offices, and healthcare providers locations to offer personalized services and items to patients.

The invention provides significant improvements in user convenience by simplifying the process of data access and management, thus enhancing patient adherence to treatment regimens, and promoting better health outcomes. Further-more, it opens new avenues for pharmacies and healthcare providers to engage with patients, offering a platform for innovative healthcare services and digital health management solutions.

DETAILED DESCRIPTION OF THE INVENTION

Figure 1:
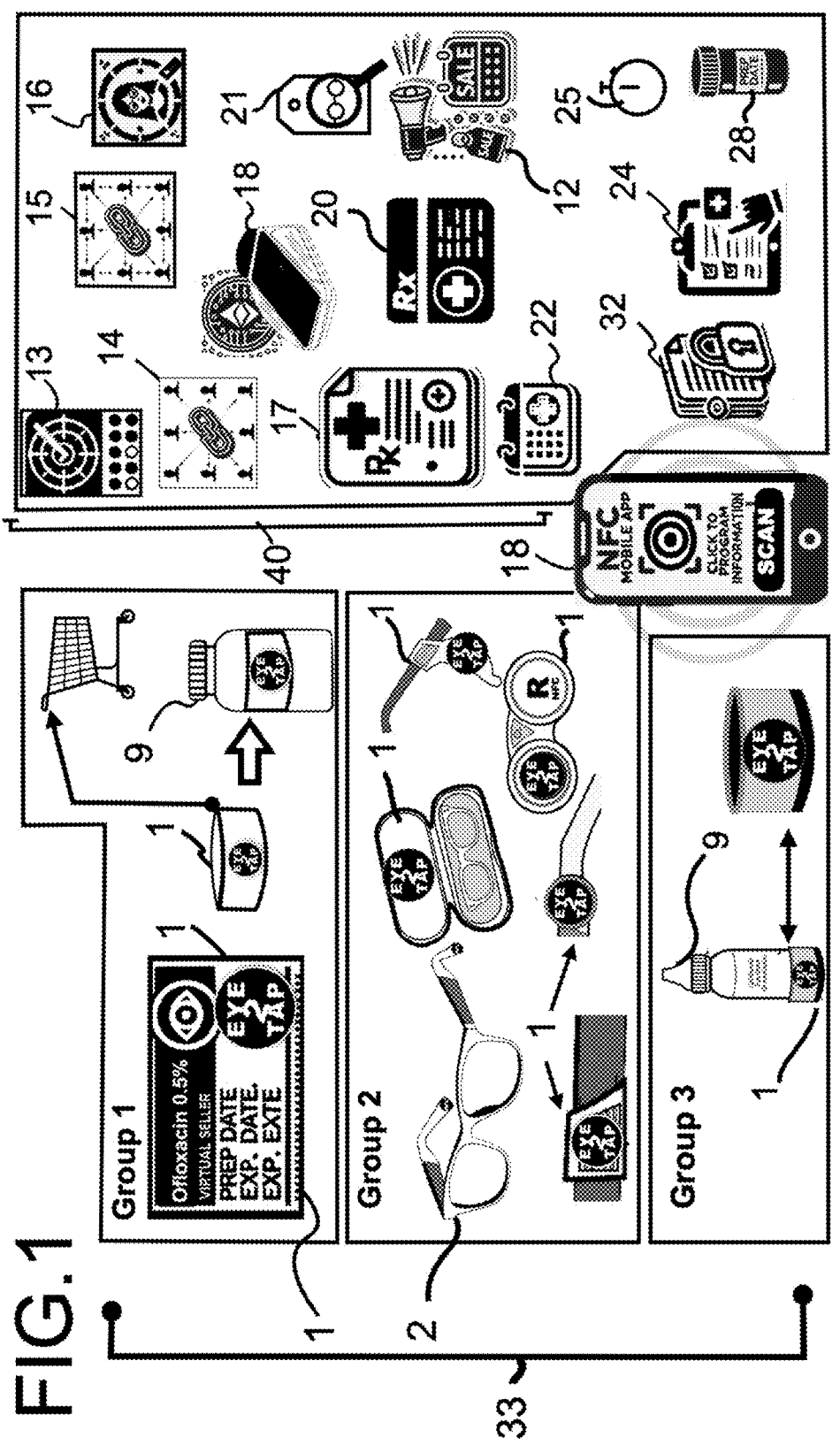
FIG. 1, The figure presents a comprehensive diagram outlining a system and method for integrating various designs of NFC adapter apparatuses onto pharmaceutical or medical items. This system details a variety of NFC adapters that can be either embedded or adapted to the product. The right side of the diagram displays the programming capabilities of data and content onto the removable, attachable NFC adapter tailored for medical and pharmacy items. The Left section illustrates silicone or plastic bands suitable for use on medication containers such as pill bottles, while other designs include bottom caps akin to what are known in some contexts as stubby holders-plastic, silicone, fabric, or foam sleeves designed to thermally insulate a beverage container, like a can or bottle. Additionally, some adapters can include decorative elements for eyewear or cases, among other items.

In accordance with various embodiments of the present invention, a versatile Near Field Communication (NFC) adapter 1 is described, capable of being programmed with a diverse array of data 40 types to enhance user interaction and functionality across a spectrum of pharmacy items 33. The Eye2tap™ NFC adapter apparatus 1 is designed to store and transmit patient-specific therapeutic directives, quantitative pharmacological specifications, and biometric tracking parameters, thus facilitating personalized medical treatment and health monitoring. In some embodiments, the adapter additionally supports promotional and marketing data, consumer loyalty incentives, and electronic prescription storage, which collectively serve to enhance the engagement and retention of healthcare service users.

Moreover, the invention may include capabilities for the provision of hyperlinked digital resources, digital asset tokens 18, non-contact payment 18, verification of product authenticity, decentralized data access points for secure data retrieval, and secure transaction records. These functionalities aim to streamline healthcare processes, improve patient compliance, and foster a more interactive and informative user experience. In certain embodiments, the NFC adapter 1 also enables the facilitation of communication through embedded communication facilitation mechanisms, providing direct links to virtual healthcare services and enhancing the overall efficiency of healthcare delivery. This broad spectrum of potential applications underscores the adaptability of the NFC adapter 1 to meet various user needs and evolving technological landscapes in healthcare and retail environments.

The invention is a removable and attachable Near Field Communication radio module adapter apparatus 1 designed specifically for use with medication containers 9, retail items and medical items 33. This radio adapter 1 can be securely attached to any part of a medication container 9, enhancing its functionality by embedding it with NFC technology. This enables the container 9 to communicate with NFC-enabled devices such as smartphones or tablets.

In the context of this description, the terms "one embodiment," "an embodiment," or "embodiments" signify that the mentioned feature or features are present in at least one embodiment of the invention. It should be noted that separate mentions of "one embodiment," "an embodiment," or "embodiments" do not necessarily pertain to the same embodiment and are not mutually exclusive unless explicitly indicated or as would be apparent to those skilled in the art from the description. For instance, a method, feature, structure, act, or the like described in one embodiment may also be present in other embodiments but is not mandatory. Consequently, the present invention encompasses various combinations and/or integrations of the embodiments detailed herein.

In one embodiment, the Eye2tap™ NFC adapter apparatus 1 is to provide a seamless and efficient method for transmitting a variety of important information to users 10. This information includes, but is not limited to, healthcare provider prescriptions, medication usage instructions, loyalty points 18, prescriptions 17, detailed product information 21, healthcare provider appointment scheduling 22, and virtual audio telemedicine connections 16. The adapter 1 is programmed through a smartphone mobile application 18, which can be accessed and manipulated in various settings like online optical stores, healthcare offices, or at any participating business.

In one embodiment, the description of the system and method for this invention, the term "user" 10 refers to both customers and patients who interact with the NFC-enhanced medication containers or adapters 9. By tapping or scanning the NFC adapter 1 attached to these containers 9, the user is linked to a variety of information tailored to enhance their healthcare experience. This includes medication usage instructions, medical data 20, health data 13, retinal imaging 14, loyalty programs 71, promotional flyers 14, healthcare provider scheduling options 16, websites 14, and audiovisual telemedicine connections 16.

Referencing FIG. 1, the right column of the diagram 40 provides a detailed depiction of the programming areas applicable to the NFC adapter apparatus 1. These areas are designated for the storage 39 and transmission 39 of a wide range of data types, each tailored to enhance user experience and functional utility of the associated selected items 33. Specifically, the programmable functionalities include:

Patient-specific therapeutic directives 25: Instructions for the administration and timing of pharmaceutical treatments.

Quantitative pharmacological specifications 28: Data specifying amounts and frequencies of medication intake tailored to individual needs.

Biometric tracking parameters 13: Metrics related to the monitoring of physiological or health-related metrics over time.

Promotional and marketing data 12: Information related to promotional campaigns, discount offerings, or commercial incentives linked to health items 33 or services.

Consumer loyalty incentives or non-contact payment 18: Details regarding rewards and incentives designed to enhance customer retention, non-contact credit card payment and engagement.

Electronic prescription storage 20: Digital storage of medical prescriptions for ease of access and reference.

Detailed product descriptors 21: Comprehensive information about medical or pharmaceutical items 33 including specifications and usage which may include loss and found information.

Healthcare scheduling facilitation 22: Digital tools for arranging and managing appointments with medical professionals.

Virtual healthcare linkage 16: Digital interfaces for remote health consultations and services.

Provider and institution data 20: Informational content about healthcare providers or medical facilities.

Hyperlinked digital resources 14: Web-based links to supplementary information, resources, apps or online services.

Digital asset tokens 18: Minted digital assets for verification of authenticity or ownership, applicable to items 33 or services.

Decentralized data access points 15: Links to a peer-to-peer file system for enhanced data security and permanence.

Secure transaction records 32: Encoded data to secure and record transactions or interactions.

Transparent record-keeping systems 15: Systems for maintaining accessible, secure logs of data across distributed networks.

Communication facilitation mechanisms 16: Links and protocols to enable direct communication through audio or visual digital mediums.

In one embodiment, the arrangement is part of a broader patient or customer retention strategy that utilizes the NFC adapter apparatus 1 to deliver comprehensive, targeted content directly to the user 10. The presentation and utilization of this technology are designed not just to inform but also to engage users actively, thereby enhancing patient compliance and satisfaction. Instead of fragmenting the innovations into multiple separate patent filings, this document consolidates them into a single comprehensive application. This approach underscores the synergistic nature of the NFC adapter apparatus 1, combining multiple functionalities and user engagement techniques into a unified system that enhances the overall utility and effectiveness of traditional medication containers 9.

In one embodiment, the explanation of this invention, the term "user" 10 denotes both customers 10 and patients 10 who interact with our NFC-enabled medication containers 9 or pharmacy items 33 1. By tapping or scanning the NFC adapter apparatus 1 attached to these containers 9, users can instantly access a variety of tailored information, including medication usage details, medical data 7, loyalty program options, promotional materials, healthcare provider scheduling information 22, and links to websites 12 and audio-visual telemedicine services 16.

Certain embodiments may provide, implementation may be a key to a strategic approach aimed at patient retention, leveraging the NFC adapter 1 to actively engage users by providing relevant and targeted information directly through their personal devices 11. The comprehensive nature of this interaction not only informs but also improves user engagement and adherence to healthcare guidelines. By consolidating these innovative features into a single patent document, we emphasize the integrated approach of the invention, which combines multiple functionalities into a coherent system designed to enhance the practical utility of medication containers 9 for both users 10 and healthcare providers. Certain embodiments may provide a section of the invention detailing the integration of Near Field Communication (NFC) chips into a specially designed adapter apparatus 1 that may be utilized with pharmacy items 33, shopping carts, medication containers and other items sold in pharmacies. The NFC adapter 1 facilitates the communication between NFC processing devices and the pharmacy items 33 by providing a means to transmit information efficiently.

In one embodiment, the NFC adapter 1 may be encased in durable materials suitable for the retail or medical environment, ensuring the longevity and reliability of the NFC chip or hybrid chip associated with the adapter 1. These adapters 1 are designed to be easily attached to or integrated within pharmacy items 33, allowing for a straightforward method to deliver and access information such as medication guidelines, patient records, or promotional content directly through a compatible NFC processing device.

In one embodiment, the NFC adapter 1 housing may be constructed from silicone or other materials, which can incorporate designs for promotional, marketing, engineering or decorative purposes, and may also include anti-slip features.

In another embodiment, the NFC adapter 1 may incorporate a magnetic component, enabling it to attach to magnetized surfaces such as refrigerators or other metallic objects.

In another embodiment, the NFC adapter 1 may incorporate a design to with interference does not compromise the use of the adapter.

In another embodiment, the housing of the NFC adapter 1 may be designed with a phosphorescent material to enhance visibility in low-light conditions or at night.

In another embodiment, the NFC adapter 1 may include additional electronic sensors to detect movement or placement.

In another embodiment, the NFC adapter 1 may feature a designated area where personal information or data can be imprinted, either digitally or through non-digital means such as hospital uses.

In another embodiment, the NFC adapter 1 may be designed to be removable and transferable to other items 33.

In another embodiment, the NFC adapter 1 may serve dual purposes, functioning with both eyeglasses and medication containers.

In another embodiment, the NFC adapter 1 may be configured to communicate with vehicle or computer systems to activate commands.

In another embodiment, the NFC adapter 1 may incorporate materials designed to prevent electromagnetic interference.

In another embodiment, the NFC adapter 1 may include an additional housing to accommodate other sensors or devices for tracking and search capabilities.

In another embodiment, the NFC adapter 1 may include a device capable of facilitating lost and found functionality.

In one embodiment, the NFC adapter 1 may integrate temperature sensors to ensure that medications, particularly those that are temperature-sensitive, are stored correctly. This integration would enable real-time temperature tracking and generate alerts to the patient or pharmacy if the medication is exposed to unsafe temperatures.

In another embodiment, the NFC adapter 1 may assist with temperature control by incorporating insulating materials. This insulation helps to maintain the medication within the recommended temperature range, ensuring its efficacy and safety. In another embodiment, the NFC adapter 1 can be programmed to monitor the expiration dates of medications and send reminders to users or pharmacists as the expiration date approaches. This functionality helps to prevent the usage of expired medications and ensures timely replenishment.

In another embodiment, NFC adapter 1 may include a system for logging when a medication container is opened. This feature assists in monitoring patient adherence to their prescribed medication schedules, with the logged information being transmitted to healthcare providers for enhanced patient management In another embodiment, the NFC adapter 1 may include a GPS capability. In another embodiment, the NFC adapter 1 may include one or more temperature sensors. In another embodiment, the NFC adapter 1 can be configured to link to interactive, multimedia guides that provide comprehensive instructions on medication usage, potential side effects, and other critical information. These guides can include video tutorials, audio instructions, or interactive FAQs.

In another embodiment, the NFC adapter 1 may incorporate anti-counterfeiting measures to verify the authenticity of the medication, ensuring that patients receive genuine items 33. This feature is particularly valuable in combating the distribution of counterfeit drugs. In another embodiment, the NFC adapter 1 may incorporate a connection interface for a transcranial adapter or types of neuro-linking type technologies.

In another embodiment, the NFC adapter 1 can log data about medication usage patterns. This logged data can be analyzed to provide insights into patient behavior, medication efficacy, and potential side effects, with reports being sent to healthcare providers or researchers.

In another embodiment, the NFC adapter 1 may be configured to interact with smart home devices, such as issuing reminders through smart speakers or integrating with smart lighting systems to signal medication times.

In another embodiment, the NFC adapter 1 can facilitate connections to support groups or social networks for patients with similar conditions, providing a platform for sharing experiences, advice, and support.

In another embodiment, the NFC adapter 1 may streamline virtual healthcare services by linking directly to telemedicine platforms, enabling patients to access remote consultations and share real-time health data with their providers.

In another embodiment, the NFC adapter 1 can securely store personal health records, allowing patients to carry their medical history and share it with healthcare providers when necessary.

In another embodiment, the NFC adapter 1 may serve as vehicle, work or home key.

In another embodiment, the NFC adapter 1 may be associated with a type of cryptography.

By simplifying the interaction process, users need only to wave, scan, or tap their NFC processing device near the adapter-equipped items 33 to engage with the content programmed 50 into the NFC chips 27. This technology significantly enhances the user experience in pharmacies or medical practices by streamlining the information exchange and improving the accessibility of vital medical data and pharmacy services.

Certain embodiments may provide, the description of this invention, the term "scan" refers to the interaction, either by waving or tapping, with an NFC-compatible processing device over an NFC adapter apparatus 1. In this context, NFC tags 1 are understood to be part of a removable and attachable NFC adapter apparatus 1 designed specifically for use with pharmacy items 33 such as medication containers 1200, medical items, and/or shopping carts.

Our system and method leverage these NFC adapters 1 to facilitate easy access for users (customers or patients) to a variety of programmed information. The NFC adapters 1 can be made from various materials, including but not limited to plastics, metals, or any suitable composites.

In another embodiment, the housing design of some adapters may be manufactured using 3D printing technology or molded into complex three-dimensional designs to accommodate specific aesthetic or functional needs.

In another embodiment, setup allows users with NFC-compatible devices 50 to access diverse types of data through the NFC adapter links, including video/audio communications, mobile application links, websites (via Internet Protocol URL links), blockchain smart contracts, distributed acyclic graphs ledger, distributed ledger technology history 15, cryptocurrency addresses, tokens, transaction hashes, and IPFS (Interplanetary File System) links.

Certain embodiments, the use of IPFS as a peer-to-peer file system designed to enable decentralized information sharing across a network of computers without requiring mutual trust among the nodes. By integrating IPFS with the NFC technology embedded in our adapters 1, we provide a novel method for transferring decentralized information relevant to both healthcare and non-healthcare sectors.

In some embodiments, the removable attachable NFC adapter apparatus 1 also called EYE2TAP™, which may be attached or embedded onto medication containers 1200 or medical items, may be utilized across a variety of pharmacy items 33. These items 33 are primarily used to facilitate the distribution of healthcare provider information, prescription details, marketing materials, brand awareness, and to enhance the connection between eye doctors, healthcare provider offices, optical chain stores, and their patients or customers. The NFC adapter 1 is a near-field communication device that can be pre-programmed using NFC writing technology.

Given that most new smartphones, currently in the market are equipped with NFC capabilities that can read and write to NFC technology, this method allows for easy programming and information access. Although some smartphone models may require an additional mobile application to interact with NFC technology, these apps are readily available in app stores, simplifying adoption. This convenience supports widespread use in various settings, including optical chain stores, optometrist offices, healthcare provider offices, supermarkets, and pharmacies, enhancing the method of information transfer through NFC technology.

In some embodiments, the NFC adapters 1 mentioned may be pre-programmed with a unique Universal Resource Locator (URL) and/or IPFS (Interplanetary File System) addresses using a mobile application or software. Unlike traditional methods where data retrieval is based on location, IPFS files are accessed based on their content. The defi methodology, involves utilizing NFC technology combined with IPFS to create a hybrid network of centralized and decentralized nodes 15. These nodes can be various computing devices such as personal computers, smartphones, or laptops, each capable of sending and receiving data. This system is designed to remove reliance on a centralized server, instead distributing data across a network that includes both centralized and decentralized nodes.

In some embodiments, the methodology and system described in our patent includes using the web or IPFS technology to deliver information like healthcare provider prescriptions, eyewear prescriptions, advertisement coupons, medication instructions, and loyalty program details via programmed NFC adapters attached to pharmacy items 33. This approach allows for a flexible integration of centralized 14 and decentralized systems 15, which can retrieve and share data via IPFS 15. The technology ensures that information such as healthcare details, promotional content, and prescription data can be easily shared and accessed globally through a simple scan of an NFC-enabled device over the NFC adapter on the relevant items 33. This method enhances the efficiency and accessibility of information distribution in healthcare and retail environments.

In some embodiments, the NFC adapter apparatus 1 may serve as a multi-innovative solution for enhancing the user interaction, but also as an accessory for support and functionality of pharmacy or medical items 33, such as medication containers and reading glasses. The apparatus, designed as a cover, band, or adaptable accessory, incorporates an NFC (Near Field Communication) or hybrid RFID apparatus module 1 equipped with a digital identification tag.

In some embodiments, the NFC adapter apparatus 1 may serve as an adaptive solution for enhancing the shopping carts in pharmacy or retail location 33. The apparatus, designed as a cover, band, or adaptable accessory, incorporates an NFC (Near Field Communication) or hybrid RFID apparatus module 1 equipped with a digital identification tag.

In accordance with further embodiments of the invention, the apparatus with identification tag 1 is programmed to store critical data or content pertinent to the pharmacy item it is attached to, including but not limited to medication dosages, expiration information, user-specific prescriptions, and operational settings for devices like reading glasses or any eyewear. When the NFC-equipped pharmacy or medical items 33 come within proximity of an NFC-enabled mobile device 50, the tag 27 transmits this data to the device, facilitating immediate access to important product details, usage instructions, and compliance information directly through an associated mobile application.

Figure 5:
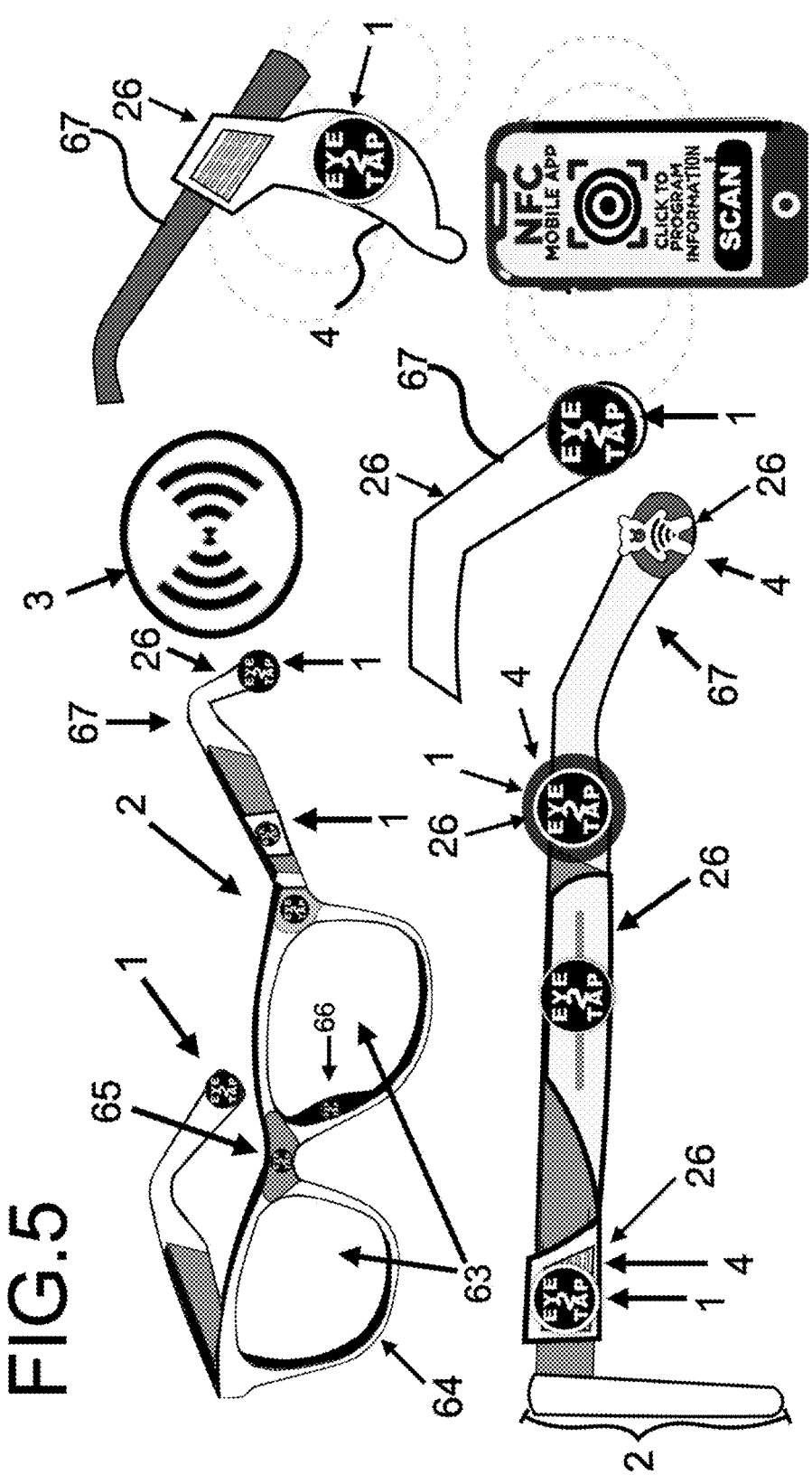
FIG. 5. The disclosed embodiment features eyewear accessory for eyewear, such as sunglasses and eyeglasses, equipped with an NFC adapter apparatus that can be strategically positioned on any part of the frame, tailored to both aesthetic and functional needs. This NFC adapter is designed to be discreet yet easily accessible, integrated into various frame components like the temples, bridge, or corners, ensuring NFC technology is incorporated seamlessly without affecting the eyewear's style or comfort.

FIG. 5: Embodiment of NFC-Enabled Eyewear: The present disclosure encompasses an embodiment of eyewear, including sunglasses 2 and eyeglasses 2, wherein each frame is enhanced with an embedded or adaptable Near Field Communication (NFC) adapter apparatus 1. This embodiment illustrates the strategic placement of the NFC adapter 1 on any feasible segment of the eyewear 2 frame, dictated by aesthetic or functional design preferences by manufacturer, retail or user.

In one embodiment, the NFC adapter apparatus 1 may be engineered to be discreet yet accessible, integrated into various components of the eyewear structure 2 such as the temples 67, the bridge 65, or even the frame corners, depending on design specifications and user accessibility. This flexibility in placement allows for seamless integration of NFC technology 1 without compromising the style or comfort of the eyewear 2.

In some embodiments, the NFC adapter apparatus 1 may serve as conjunction with eyewear 2 structure comprise a manufacturer unique eyewear enhancement system or as an embedded adapter system.

In some embodiments, the NFC apparatus 1 may be programmable for various functionalities, the NFC adapter 1 on the eyewear may store and transmitting specific information upon interaction with an NFC-compatible device, such as a smartphone. By simply scanning or tapping the NFC-enabled segment of the eyewear frame with an NFC-compatible smartphone, the user is instantly provided with digital content. This may include, but is not limited to, directing the smartphone's browser to a specific webpage, triggering the download, or opening of a mobile application, or linking to a user interface designed for interactive settings for a secondary electronic device.

The integration of NFC technology 1 into eyewear frames offers a novel method of information sharing and interaction, enhancing the utility of traditional eyewear. This capability transforms the eyewear into a dynamic tool that can provide educational content, promotional links, or personalized user experiences, thereby adding significant value to conventional optical items 33.

In some embodiments, the radio module 27 could be a near-field communication (NFC) module 1, such as a hybrid, mixed NFC/RFID, Near field communication or Radio field identification chip, multi radio module 1. This module might take the form of a transponder or a radio label, like an active, passive NFC 27, hybrid tag 27, or RFID tag 27.

In accordance with further embodiments of the invention, the integration of one or more type of NFC chip 27 technologies in the apparatus may enhance its capabilities. The NFC technology adapters 1 within these pharmacy items 33 enables several advanced functionalities aimed at improving patient safety, compliance, and convenience.

Figure 3:
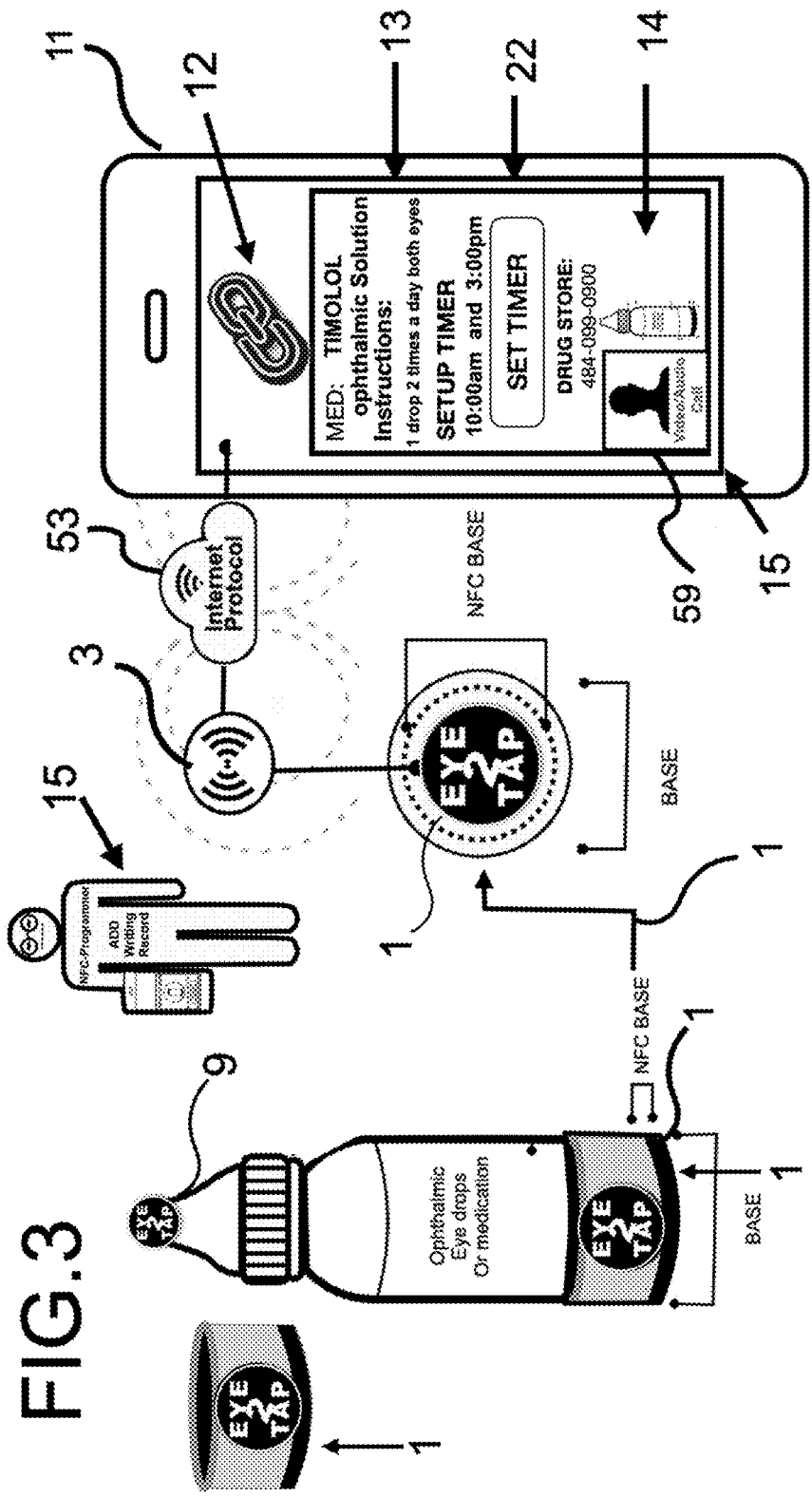
FIG. 3 The figure delineates various material apparatus designs that are applicable for employment on containers for medications, such as bottles intended for eyedrop medications. Further, the diagram includes alternative designs that feature bottom caps, like entities commonly identified as stubby holders. These caps are constructed from materials including of any material and are engineered to cover a part of the containers, for example, eyedrop medication containers and pill medication containers.
Figure 4:
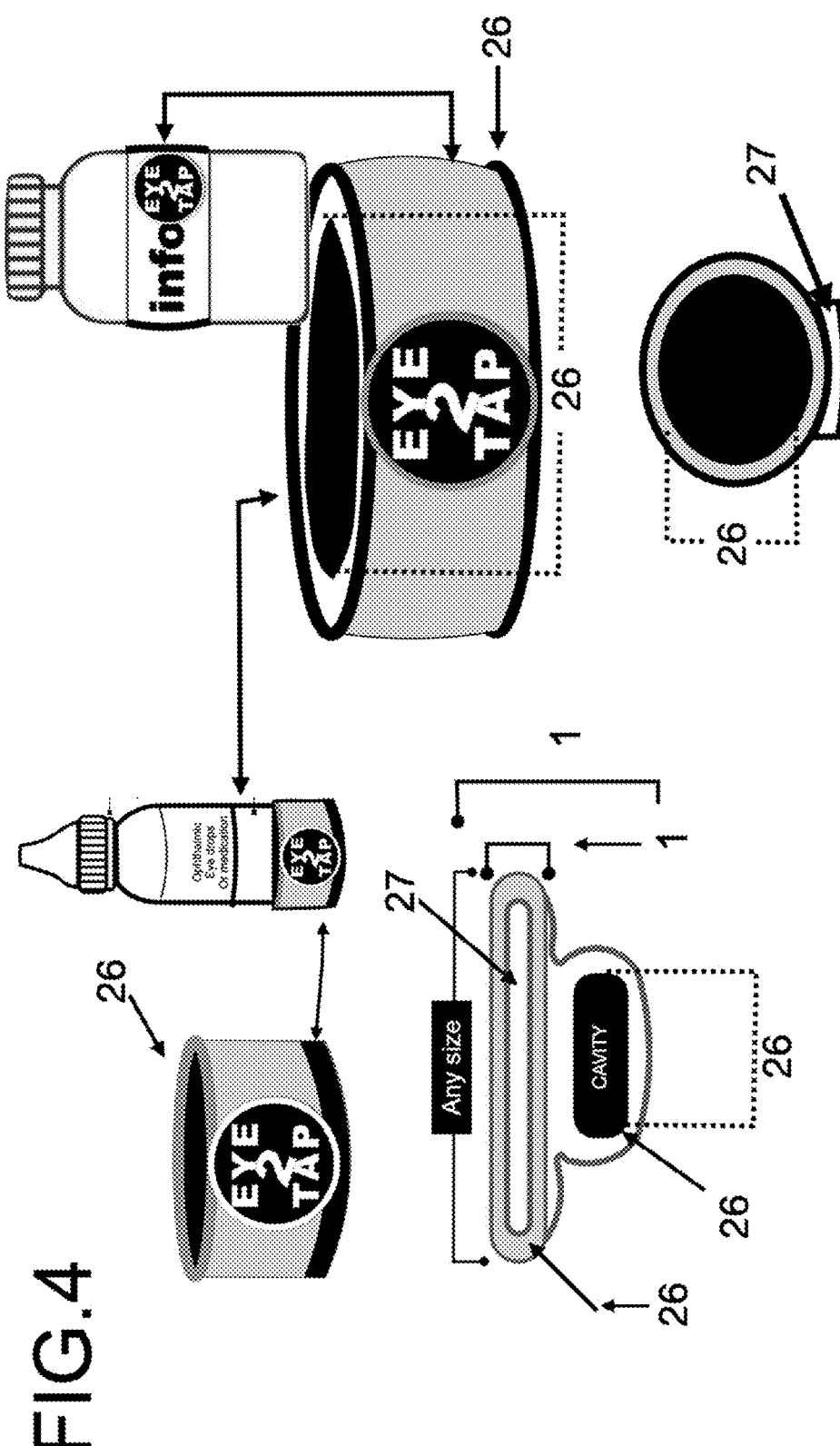
FIG. 4. The present disclosure illustrates various embodiments of the Eye2tap™ NFC adapter apparatus, each engineered to integrate seamlessly with a broad spectrum of containers designated for the storage and dispensing of medicinal items. As delineated in the depicted configurations, these embodiments encompass adaptable and interchangeable designs, facilitating a universal application across diverse container formats typically utilized within pharmaceutical, retail, or medical contexts.

In some embodiments, the NFC adapter 1 may interact with one or more mobile applications to set reminders for medication intake 22, track dosage history 13, and alert users about potential medication interactions or refills 14 as seen on (FIG. 3).

In one embodiment, in cases involving electronic reading glasses, an NFC apparatus 1 or tag 27 can automatically adjust settings such as magnification, tint and lighting based on the user's preset preferences stored within the identification tag 27. This personalized approach not only enhances the usability of pharmacy items 33 but also supports better health outcomes through improved adherence to medical guidelines and personalized product interaction.

In one embodiment, in cases involving electronic prescription eyeglasses or sunglasses lens technologies, an NFC apparatus 1 or tag 27 can automatically adjust settings such as magnification, tint and lighting based on the user's preset preferences stored within the identification tag. When mentioning lens technology, we are talking about sensors built into the lenses of eyeglasses or sunglasses that might be called smart glass technology. Where the electrical stimulation can cause one or both lenses to become tinted, translucent for amblyopia, or even change of index of refraction or power as smart liquid lens technology.

In one embodiment, the apparatus can include the following features: The eyeglasses or sunglasses are equipped with an NFC apparatus 1 that stores user-specific preferences at least one of: magnification, tint, and lighting settings.

In one embodiment, the NFC apparatus 1 may communicate with the eyewear to automatically adjust these settings when the glasses are worn. The eyewear includes mechanisms for adjusting the magnification based on the user's stored preferences, allowing for automatic correction of vision as needed.

In other embodiment, the NFC apparatus 1 may communicate with lenses to become tinted in response to electrical signals, providing protection against bright light or sunlight and enhancing visual comfort. They can also be adjusted to become translucent to assist in the treatment of amblyopia (lazy eye), managing the condition by selectively altering the transparency of the lens.

In other embodiment, the NFC apparatus 1 may communicate with lenses that incorporate smart liquid lens technology, allowing them to change their index of refraction or power dynamically, enabling automatic adjustment of their focusing power for optimal vision correction.

In other embodiment, the NFC apparatus 1 may communicate with sensors embedded within the lenses to detect environmental conditions and user activity, triggering necessary adjustments in magnification, tint, or translucence based on the preset preferences stored in the NFC tag 27. The lenses are designed to respond to electrical stimulation, inducing changes in tint, translucence, and refractive index, thus allowing real-time adaptation of the eyewear to varying conditions.

In accordance with further embodiments of the invention, other methodologies of use may include any decentralized system 15 or distributed ledger technology 15 use.

In other embodiment, the NFC apparatus 1 may be used with IPFS (Inter-Planetary File System) 15 operations. Wherein having one or more computer nodes store parts of files, allowing for data retrieval from multiple nodes instead of a single location. This decentralized system enhances data accessibility and resilience, making it a unique use the NFC technology, particularly when combined with traditional centralized systems and URL linking 14.

The accompanying illustration (FIG. 2) depicts an embodiment, methodology of programming information onto an NFC adapter 1 by a programmer 10 whether a retailer, manufacturer, healthcare provider, user, optician, or employee. This programming process is crucial for enabling the NFC adapter, whether embedded or attached to pharmacy items 33 such as medication containers, to convey essential information effectively. Such information might include healthcare provider details, prescription data 17, or promotional content 21, accessible through an NFC-enabled device. This procedure illustrates the NFC adapters' 1 role in seamlessly integrating modern digital communication technologies into daily healthcare and retail activities.

In one embodiment programmer 10 who configures the NFC adapters 1 might be in a variety of settings, such as retail stores, factories, pharmacies, or even from the comfort of their own home. An individual 1, using a smartphone 50 equipped with an NFC-capable mobile application 12, may upload, and encode various types of digital links into the NFC adapters 1. These adapters can be designed in various forms, including traditional stickers, modern silicone bands, or other customizable adapters that fit around pharmacy items 33 like containers or cups.

In other embodiment, these NFC apparatus 1 bands or adapters can be designed to snugly fit above or below a container, ensuring secure attachment and easy accessibility. Attached to a diverse array of items 33 ranging from informational signs and stickers to eyewear accessories and medication containers, the programming via a mobile application can encompass at least one of: a unique identifier, URLs, minted non-fungible tokens (NFTs), IPFS addresses, transaction hashes, distributed ledger details, and other pertinent digital data 40. This functionality showcases the broad adaptability and utility of removable attachable NFC adapter technology, enabling tailored and direct access to essential information across various settings, whether in commercial environments or for personal use at home.

In other embodiments, a plurality of designs of the NFC adapter apparatus 1 may be engineered to house not only traditional NFC tags 27, NFC identification tags, radio identification tags, hybrid near field technology, multi-hybrid NFC chips or other radiocommunication technologies based on NFC standards or technologies. This capability allows the NFC adapter 1 to support a broader range of functionalities, such as environmental sensing, health monitoring, or enhanced data communication protocols, which could include temperature sensors 13, sweat glucose monitors 13, or even more complex telemetry systems. By integrating these sophisticated technologies into the NFC adapter 1, it becomes a versatile tool that can adapt to future advancements in NFC and related fields, enhancing its applicability in a wide range of pharmacy items 33 and broadening its utility in healthcare and commercial settings.

The preceding is a simplified summary to provide an understanding of some embodiments of the present invention. This summary is neither an extensive nor exhaustive overview of the present invention and its various embodiments. The summary presents selected concepts of the embodiments of the present invention in a simplified form as an introduction to the more detailed description presented below. As will be appreciated, other embodiments of the present invention are possible utilizing, alone or in combination, one or more of the features set forth above or described in detail below.

Programming Flexibility 40: In one embodiment, the NFC adapters 1 may be programmable by entities such as retailers, user, healthcare providers, or manufacturers, who utilize a mobile application with NFC communication capabilities. The content loaded onto the NFC adapters apparatuses 1 can range from static data, like prescription details 20 and healthcare provider information, to dynamic content such as promotional offers 12 and health tips that can be regularly updated to ensure ongoing relevance and engagement.

Data Types and Links 14: In one embodiment, the programmed data within the NFC adapters can include one or more unique identifiers for individual tracking and authentication:

In one embodiment, the NFC apparatus may be preset with Direct URL links 14 to access web-based resources.

In one embodiment, the NFC adapter apparatus 1 may be linked to one or more Minted non-fungible tokens (NFTs) 15 to provide ownership proof or authenticity certification.

In one embodiment, the apparatus may be linked to a IPFS links 15 for decentralized data storage and retrieval, enhancing data permanence and censorship resistance.

In one embodiment, the apparatus may be associated with a binary coding or encoding device 13.

In one embodiment, the NFC adapter apparatus 1 may be associated with at least one Transaction hash for recording secure interactions or transactions.

In one embodiment, the NFC adapter apparatus may be associated with data of a Distributed ledger information 15 system for facilitating transparent and secure record-keeping across multiple nodes.

In one embodiment, the NFC adapter apparatus may be associated with a barometric sensing device 13.

In one embodiment, the NFC adapter apparatus may be associated with a gas element sensing device 13.

In one embodiment, the NFC adapter apparatus may be associated with a magnetic sensing device 13.

In one embodiment, the NFC adapter apparatus may be associated with a electromagnetic radiation device 13.

In one embodiment, the NFC adapter apparatus may be associated with a gravitational sensing device 13.

In one embodiment, the NFC adapter apparatus may be associated g-force sensing device 13.

In one embodiment, the NFC adapter apparatus may be associated lumen sensing device.

In one embodiment, the NFC adapter apparatus may be associated a neutrino sensing device 13.

Potential Future Applications: In one embodiment, the NFC adapter apparatus may be linked to specification to accommodate future technological advancements and applications of NFC technology.

In one embodiment, the NFC adapter apparatus may be associated with Integration with emerging digital health technologies, such as telemedicine platforms 16 and electronic health records 17, to broaden the scope and efficiency of healthcare delivery.

In one embodiment, the NFC adapter apparatus 1 may be associated with expansion into new retail settings 12, where NFC can enhance customer experiences through personalized interactions and seamless digital transactions 18.

In one embodiment, the NFC adapter apparatus 1 may be associated with development of sophisticated data interactions, including live health monitoring and feedback loops between patients and healthcare providers.

In one embodiment, the NFC adapter apparatus 1 may be associated with application in global supply chains 15 14 to verify the authenticity of items 33 and secure distribution channels from manufacturers to consumers.

In one embodiment, the NFC adapter apparatus 1 may be associated with a system where an attachable and removable NFC adapter apparatus 1 is integrated with pharmacy items 33, facilitating diverse interactions via NFC-enabled smartphones. Users can simply scan or tap the NFC adapter with their smartphone to access or upload critical data such as healthcare provider prescriptions 17, telemedicine connections 16 for visual and audio calls, and detailed information about eyewear products 33 including spectacles and accessories. Each adapter 1 includes a unique identifier and can also direct users to specific business websites, web 3, web 4, AI technologies.

In one embodiment, the NFC adapter 1 may designed with a housing 26 that is specifically tailored to fit and multifunction seamlessly with various pharmacy items 33. This housing allows the NFC adapter 1 to be securely attached or easily removed as needed, ensuring versatility across different items in a pharmacy setting. The information transfer is enabled through programming stored on the NFC tag 27 within the adapter, which can be managed via decentralized systems or a central server, according to the specifics of this patent.

In one embodiment, the programming methods for the NFC adapter 1 can vary, allowing for tailored information delivery that might include healthcare services, product marketing 21 12, or both 40.

In one embodiment, the approach may also incorporate a sophisticated marketing strategies 12 through the NFC adapters apparatus 1, including the use of minted non-fungible tokens (NFTs) 15 for advanced marketing techniques, loyalty programs 18, and promotional strategies 14.

In one embodiment, the approach may also incorporate a sophisticated marketing strategies 12 using data of the user 10.

In one embodiment, the approach may also include examples of practical application including using URLs 14 that are programmed into the NFC apparatus 1. These URLs 14 may guide users to a desired website or service and may include deep linking capabilities and mobile app integration, allowing straightforward navigation directly from the NFC interaction.

In one embodiment, the approach may also include the setup to supports telemedicine connections through specified apps, enhancing the utility of the NFC adapter 1 in providing comprehensive healthcare and retail solutions.

In one embodiment, the approach may also include examples further extend to utilizing video/audio calling app links such as https://wa.me/1111X111111, where https://wa.me/<phone number> utilizes a standard communication phone number format for initiating calls. This capability is facilitated by programming the NFC apparatus 1 with specific website links that are integrated into the messaging system.

In one embodiment, in the context of utilizing the IPFS (Interplanetary File System), an example might be:
https://IPFS.io/IPFS/
QmbxhUxsKSsDjonPXsp5Cz7KxUJmPNoBkBtqMqMzZ4PX5Rimage.png, where the link includes a hash code representing content-based addressing, and the image or page PNG serves as the file that identifies the data on decentralized servers over the IP.

Future applications and adaptability of removable NFC Technology: In some embodiments, the NFC adapter apparatus is designed to house various types of NFC technology, including passive NFC, active NFC, or potentially new hybrid NFC chips 27 that enhance current capabilities. These adapters 1 are uniquely tailored to fit onto or within pharmacy items 33, ranging from medication containers to any other item sold in pharmacies. The design of the housing 27 1 may also be customized, potentially using 3D modeling 33 to fit specific pharmacy items 33, ensuring seamless integration and functionality. Future applications could include interactive applications and audio/video 16 connections that extend the utility of NFC technology.

Smartphone Integration and User Interaction 50: In some embodiments, most smartphones on market are equipped with NFC capabilities, allowing them to interact with NFC technology and can work with the adapters 1 by using a mobile application specifically designed for data communication, storage, or display of content related to the information on the NFC tag 27 1. As illustrated in FIG. 1, users can program the NFC tags 27 via a mobile application, with the programming options varying depending on the tags and the specific items 33 involved. Any individual with a mobile device that runs the NFC programming application can become a programmer, facilitating diverse and versatile interactions with NFC-equipped items 33.

Interaction Protocols and Information Access: In some embodiments, a programmer and user may utilize portable electronic devices such as smartphones to write to or read from the NFC apparatus 1. Users 10 can also use their smartphones to connect with centralized servers or decentralized nodes, enhancing the flexibility of information access. Once a company or programmer has configured their selected NFC-enabled pharmacy items 33 with the necessary information and connection links 40, they can specify how each product should interact with users. This enables users to access the information programmed into the NFC apparatus 1 by the programmer's device 50, creating a robust information exchange ecosystem.

Programmability and Online Connectivity: In some embodiments, turning to FIG. 2, we detail a scenario involving pharmacy items 33, such as medication containers, health monitors, or medical accessories, each equipped with an NFC apparatus 1. These items 33 can be programmed by a programmer using an NFC application to incorporate various digital resources.

In some embodiments, the potential programing of the content includes mobile apps 7, URL links, video/audio telemedicine connections, NFT-based coupons, or vouchers 18, medication prescriptions 17, and more. The NFC functionality within these items 33 also supports the programming of web-based databases or links to specific transaction hashes, smart contracts 15, IPFS links, and online prescription 17 databases to verify authenticity and prevent fraud.

Utilization of programmed removable attachable NFC adapter apparatus 1: In some embodiments, turning to FIG. 2, we detail a scenario involving pharmacy items 33, such as medication containers, health monitors, or medical accessories, each equipped with an NFC tag apparatus 27 1. These items 33 can be programmed by a programmer 10 using an NFC application to incorporate various digital resources. Potential programmable content includes mobile apps, URL links, video/audio telemedicine connections, NFT-based coupons, or vouchers 18, medication prescriptions 17, and more. The NFC functionality within these items 33 may also supports the programming of web-based databases or links to specific transaction hashes 15, smart contracts 15, IPFS links 15, and online prescriptions 7.

In some embodiments, the information programmed 40 onto the NFC tags 27 housed within the removable apparatus 1 enables the establishment of online connections for functionalities such as redeemable NFT or image-based coupons, telemedicine connections via video/audio, medical appointment scheduling links 22, and NFT-based healthcare provider service coupons 18 and vouchers 14 18. Users can store these coupons in an NFT wallet, which can be redeemed at various healthcare facilities including pharmacies, medical labs, and clinics, demonstrating the expansive and practical applications of NFC technology in the healthcare sector.

In some embodiments, the NFC adapter apparatus 1 may be a at least one of a removable apparatus, a housing apparatus, attachable apparatus, a modular multi-fit apparatus, eyewear accessory apparatus, a tactile writing or reading system used by people who are visually impaired, 3D printable apparatus, a dropper apparatus, medication temperature regulating apparatus, a vehicle sensor apparatus, door key apparatus, membership apparatus, contactless payment apparatus, a smart hub apparatus, vehicle apparatus, decorative apparatus, medical data transferring apparatus, a lighting apparatus, sensor apparatus, shopping attachable apparatus, private key apparatus, ophthalmic apparatus, haircut apparatus, finance apparatus, logistic apparatus, speech to text activation apparatus, text to speech activation apparatus, waste management apparatus, education apparatus, tourism apparatus, inventory apparatus, biometric apparatus, marketing apparatus, robotic apparatus, magnetic field sensing.

Advanced Hybrid NFC Chip Technologies 27: In some embodiments, turning to FIG. 2, we detail a scenario involving pharmacy items 33, such as medication containers, health monitors, or medical accessories, each equipped with an NFC adapter apparatus 1. These items 33 can be programmed by a programmer using an NFC application to incorporate various digital resources. Potential programmable content includes mobile apps, URL links, video/audio telemedicine connections, NFT-based coupons, or vouchers 18, medication prescriptions 17, and more. The NFC functionality within these items 33 also supports the programming of web-based databases or links to specific transaction hashes, smart contracts 15, IPFS links, and online prescriptions.

In some embodiments, the NFC adapter apparatus 1 may be designed to accommodate a wide range of NFC technologies, including innovative hybrid NFC chips 27 1 that integrate additional functionalities to meet evolving needs. These advanced chips could include sensors capable of analyzing biological markers such as sweat, saliva, or tear osmolarity, which could be crucial for medical diagnostics and monitoring. For instance, specific hybrid NFC chips may incorporate sensors that detect glucose levels directly from sweat, offering non-invasive alternatives for diabetes management.

Figure 2:
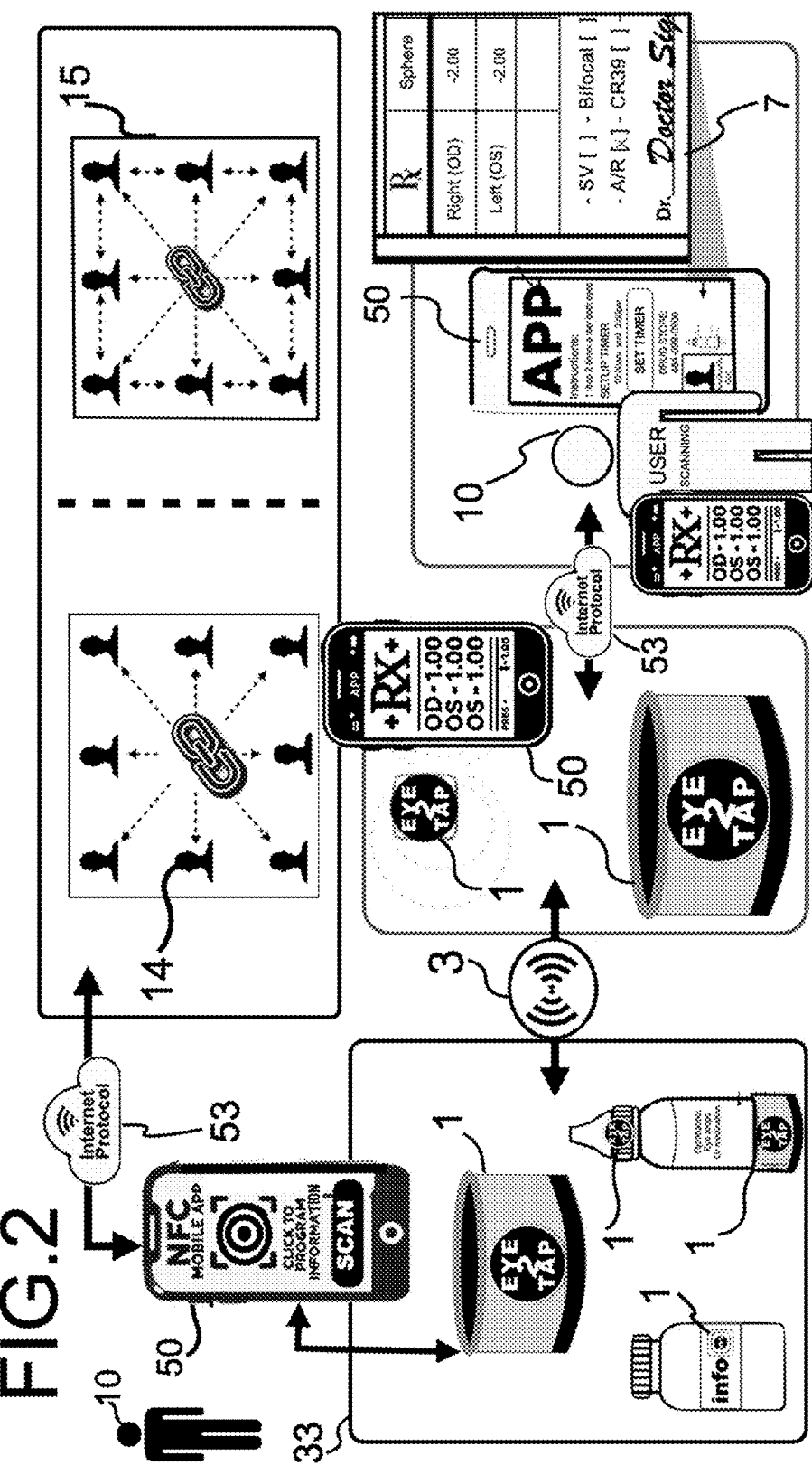
FIG. 2 The depiction provides an outline of a workflow, system, and method for user-driven uploading of data and content information, as described in one embodiment of the disclosure. The adapter apparatuses are designed for use with medical and pharmacy items, including medication containers.

In some embodiments, in FIG. 1 and FIG. 2, we detail a scenario involving pharmacy items 33, such as medication containers, health monitors, or medical accessories, each equipped with an NFC apparatus 1. These items 33 can be programmed by a programmer using an NFC application to incorporate various digital resources. Potential programmable content includes mobile apps, URL links 14, video/audio telemedicine connections 16, NFT-based coupons 18, or vouchers 18, medication prescriptions 17, and more. The NFC functionality within these items 33 also supports the programming of web-based databases 14 or links to specific transaction hashes, smart contracts 15, IPFS links 15, and online medical data.

In some embodiments, the NFC apparatus 1 might be equipped with temperature sensors as hybrid systems. These sensors could be particularly valuable in the pharmaceutical sector, ensuring that medications are stored and transported within safe temperature ranges. When scanned with an NFC processing device, these sensors provide immediate feedback on whether the medication has been exposed to temperatures that could potentially compromise its effectiveness.

In some embodiments, FIG. 2 we detail a scenario involving pharmacy items 33, such as medication containers, health monitors, or medical accessories, each equipped with an NFC adapter apparatus 1. These items 33 can be programmed by a programmer using an NFC application to incorporate various digital resources. Potential programmable content includes mobile apps, URL links, video/audio telemedicine connections, NFT-based coupons, or vouchers 18, medication prescriptions 17, and more. The NFC functionality within these items 33 also supports the programming of web-based databases 14 or links to specific transaction hashes, smart contracts 15, IPFS links, and online medical prescriptions, there could be developments in hybrid RFID-NFC technologies, which would extend the reach and functionality of traditional NFC applications. This combination could enhance the range and reliability of data transmission, making it more suitable for environments where increased communication distance is necessary.

In some embodiments, in FIG. 2 we detail a scenario involving pharmacy items 33, such as medication containers 9, health monitors, shopping carts or medical accessories, each equipped with an NFC adapter apparatus 1. These items 33 can be programmed by an electronic device using an NFC application to incorporate various digital resources. Potential programmable content includes mobile apps, URL links 13, video/audio telemedicine connections 16, NFT-based coupons, or vouchers 18, medication prescriptions 17, and more. The NFC functionality within these items 33 also supports the programming of web-based databases or links to specific transaction hashes 15, smart contracts 15, IPFS links, and online prescriptions.

In some embodiments, design innovations might include NFC chips combined with apparatus designed for interoperability with different radio wave technologies, facilitating broader communication protocols across various devices and platforms. Some NFC chips might even be developed in three-dimensional configurations, enhancing their capabilities to support complex telecommunication needs and integrating seamlessly with the Internet of Things (IoT) infrastructure.

In some embodiments, advanced NFC technologies chips 1, housed within our removable attachable NFC adapter apparatus 1, promise to revolutionize how information and data are managed and utilized in healthcare, providing more dynamic, responsive, and personalized medical care solutions. As these technologies evolve, the NFC adapters 1 can be updated to house any new type of NFC chip 1, ensuring the system remains at the forefront of healthcare technology.

What is claimed:

1. An NFC adapter apparatus for enhancing pharmacy and healthcare containers, comprising:

a three-dimensional body configured to be removably affixed around a pharmacy container such as an eye-drop bottle, pill bottle or liquid vial;

the body defining a cavity or compartment configured to interchangeably receive, enclose, and allow removal and replacement of an NFC or RFID identification tag, thereby enabling reuse of the adapter apparatus across multiple communication standards and allowing tag updates without replacing the adapter;

the cavity providing electromagnetic spacing between the tag and the surface of the container to reduce signal interference from metallic or non-metallic materials of the container;

the body being composed of silicone, foam, elastomeric, or a similar flexible insulating material to reduces mechanical wear, tear, and moisture exposure, allowing to be reused on multiple containers while maintaining functional integrity;

a programming interface configured to store data and content on the dentification on tag via wireless communication with a programming device; and a data retrieval interface configured to wirelessly transmit the stored information from the identification tag to a wireless identification reader electronic device.

2. The apparatus of claim 1, wherein the flexible insulating material forms a protective barrier that resists abrasion, deformation, and moisture ingress, maintaining the electromagnetic spacing and operational integrity of the identification tag.

3. The apparatus of claim 1, wherein the identification tag is configured to perform secure contactless payment and authentication transactions when read by a compatible payment or automated wireless identification reader electronic device.

4. The apparatus of claim 1, wherein the identification tag is configured to be programmable memory configured to be updated via a mobile application interface operated by machine, retailers, healthcare providers, and manufacturers.

5. The apparatus of claim 1, wherein the identification tag is configured to include a secure data module configured to record transaction history for verifying item authenticity and ensuring secure data transmission.

6. The apparatus of claim 1, wherein the body is configured to be removably integrated with a medication container, shopping cart, eyedrops or an eyewear frame.

7. The apparatus of claim 1, wherein the identification tag is programmed with a digital hyperlink or communication code that provides access to a remote consultation or telemedicine service when scanned by an authorized device.

8. The apparatus of claim 1, wherein the identification tag support environmental sensing and enhanced data communication protocols.

9. A method for integrating a reusable adapter apparatus containing an identification tag into retail pharmacy containers, comprising:

providing an adapter apparatus having a three-dimensional body composed of silicone, foam, or similar flexible insulating material, the body defining a cavity configured to interchangeably receive either an NFC or an RFID tag, thereby enabling operation across multiple communication standards and allowing tag updates;

affixing the reusable adapter apparatus around a pharmacy container such as an eyedrop bottle, pill bottle, liquid vial, or onto an eyewear frame, so that the cavity maintains electromagnetic spacing between the identification tag and the container surface of the container or frame to reduce signal interference from metallic or non-metallic contents;

programming the identification tag within the adapter with digital data and content using a wireless identification reader electronic device;

retrieving the stored information by bringing electronic processing device within communication range of the adapter apparatus;

interfacing the adapter apparatus with a software application that facilitates programming and retrieval and wireless distribution of the stored data to authorized devices or healthcare systems inventory, authentication, or patient communication purpose; and removing and re-affixing the adapter onto a different pharmacy container for subsequent reuse without loss functional integrity.

10. The method of claim 9, further comprising:

using the NFC adapter apparatus to deliver information to users; and programming the identification tag within the adapter apparatus with one or more of hyperlinks to digital health resources, medical data, or healthcare provider information.

11. The method of claim 9, further comprising:

providing medication notification through the interface based on the programmed information, wherein the method supports improved medication adherence and patient compliance.

12. The method of claim 9, wherein the electronic processing device:

enables the programming of identification tags within the adapter apparatuses through an interface, stores data on the NFC identification tags, retrieves the stored data from the NFC identification tags via a wireless identification reader electronic device using the interface, and displays the retrieved information to the user through the interface, wherein the method facilitates secure, contactless information distribution and data access to improve user interaction with pharmacy items.

13. The method of claim 9, further comprising:

facilitating non-contact payments through the interface by interaction with the NFC identification tag, providing hyperlinks to digital health resources and healthcare provider information within the interface, enabling virtual healthcare consultations by linking to telemedicine services through the interface.

14. The method of claim 9, further comprising:

integrating data storage solutions to ensure the security and permanence of stored data;

facilitating remote health monitoring by storing and retrieving biometric data through the interface; and enabling the sharing of health data with healthcare providers through an interface.

15. The method of claim 9, further comprising:

programming data onto the apparatus, allowing customization of data types stored on the identification tag to meet specific user needs, retrieving data from the apparatus.

16. The method of claim 9, further comprising:

enabling users to scan the apparatus with their enabled electronic devices to access text to speech information.

17. The method of claim 9, further comprising:

enabling users to scan the apparatus with their wireless identification reader electronic device to access a medical prescription.

18. The method of claim 9, further comprising:

enabling users to scan the apparatus with their wireless identification reader electronic device to access a node connection.

19. The method of claim 9, further comprising:

enabling users to scan the apparatus with their wireless identification reader electronic device to access data, content, and information.

20. The method of claim 9, further comprising:

enabling users to scan the apparatus with an NFC-enabled device to initiate a secure non-contact payment transaction.

* * * * *